United States Patent
Cherukuri et al.

(10) Patent No.: US 6,224,939 B1
(45) Date of Patent: *May 1, 2001

(54) METHOD AND APPARATUS FOR FORMING AN ENCAPSULATED PRODUCT MATRIX

(75) Inventors: Subraman R. Cherukuri, Vienna; Supapong Siris, Chantilly, both of VA (US)

(73) Assignee: Fuisz International Ltd., Dublin (IE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/309,224

(22) Filed: May 10, 1999

(30) Foreign Application Priority Data

May 22, 1998 (IE) .................................................. 980395

(51) Int. Cl.$^7$ ........................................................ B05D 7/00
(52) U.S. Cl. ........................... 427/213; 264/117; 264/7; 23/313 R; 23/313 FB
(58) Field of Search ........................... 427/213; 264/117, 264/7; 23/313 R, 313 FB

(56) References Cited

U.S. PATENT DOCUMENTS

| | | | |
|---|---|---|---|
| 2,561,392 | * 7/1951 | Marshall | 117/100 |
| 2,561,393 | * 7/1951 | Marshall | 117/100 |
| 2,561,394 | * 7/1951 | Marshall | 117/100 |
| 2,648,609 | * 10/1953 | Wurster | 99/166 |
| 3,255,036 | * 6/1966 | Kramer et al. | 427/213 |
| 3,354,863 | * 11/1967 | Reynolds | 118/62 |
| 3,949,094 | 4/1976 | Johnson et al. | 426/99 |
| 4,217,851 | * 8/1980 | Biehl et al. | 118/20 |
| 4,421,669 | * 12/1983 | Brichard | 427/213 |
| 4,428,973 | * 1/1984 | Hoerner et al. | 427/3 |
| 4,519,961 | 5/1985 | Schumacher et al. | 264/4.6 |
| 4,588,612 | * 5/1986 | Perkins et al. | 427/213 |
| 4,657,784 | * 4/1987 | Olson | 427/213 |
| 4,704,330 | * 11/1987 | Moore et al. | 427/213 |
| 4,879,141 | * 11/1989 | Chatterjee | 427/213 |
| 4,935,246 | * 6/1990 | Ahrens | 427/213 |
| 5,075,138 | * 12/1991 | Tanaka | 427/213 |
| 5,200,236 | * 4/1993 | Lang et al. | 427/213 |
| 5,380,473 | 1/1995 | Bogue et al. | 264/11 |
| 5,417,153 | 5/1995 | King et al. | 99/517 |
| 5,437,889 | * 8/1995 | Jones | 427/185 |
| 5,486,363 | 1/1996 | Kiefer et al. | 424/442 |
| 5,498,447 | * 3/1996 | Nishii et al. | 427/213 |

FOREIGN PATENT DOCUMENTS

| | | |
|---|---|---|
| 0 179 943 A1 | 5/1986 | (EP) . |
| 0 423 701 A2 | 4/1991 | (EP) . |
| 2 628 014 | 9/1989 | (FR) . |
| 2 268 094 | 1/1994 | (GB) . |
| WO88/10150 | 12/1988 | (WO) . |
| WO91/17821 | 11/1991 | (WO) . |
| WO95/15821 | 6/1995 | (WO) . |
| WO96/03893 A1 | 2/1996 | (WO) . |

OTHER PUBLICATIONS

U.S. application No. 09/162,189, Fuisz et al., filed Sep. 28, 1998.

* cited by examiner

Primary Examiner—Shrive Beck
Assistant Examiner—Paul D. Strain
(74) Attorney, Agent, or Firm—John F. Levis; Richard D. Schmidt

(57) ABSTRACT

A method and apparatus provides for the formation of an encapsulated feedstock product matrix. A solid product matrix additive is spray ejected in a free-flow condition. The matrix additive is encapsulated in its free-flow condition with a matrix encapsulant. The encapsulant additive substantially solidifies in its free-flow condition to form the feedstock product matrix.

13 Claims, 4 Drawing Sheets

METHOD AND APPARATUS FOR FORMING AN ENCAPSULATED PRODUCT MATRIX

FIELD OF THE INVENTION

The present invention relates generally to a process and apparatus for forming a feedstock product matrix. More particularly, the present invention is directed to an improved method and apparatus for forming an encapsulated product matrix. The invention further relates to equipment and a process for forming an encapsulated product matrix utilizing two or more encapsulating materials, as well as combining two or more products in the encapsulated matrix.

BACKGROUND OF THE INVENTION

In certain material processing technologies such is those used in pharmaceutical and food processing, particulate feedstock material is formed as an intermediate product for use in further processing. The particles may be formed by various techniques. One technique is to spray dry eject product particles from a spray nozzle. This technique employs a spray nozzle supported within a tower. The spray nozzle converts liquid emulsions to dry powder at elevated temperatures. Conventional heated liquid emulsion is transported to the spray nozzle where it is ejected therefrom as a dry powder into a free-flow feedstream. As the heated dry powder falls in a free-flow condition, it cools and solidifies into particles. The particles may then be used for further processing in conventional material handling applications for the formation of food stuffs and pharmaceutical products.

In certain applications, there is a need to encapsulate certain feedstock products during the material handling process so as to form a product matrix. In the food processing industry, it is typically desirable to encapsulate food and bioaffecting additives such as pharmaceuticals, nutraceuticals, flavorings, colors and sugars in dissimilar food substances such as oleaginous material like fats or oils such as flavor oils. In the pharmaceutical industry, active drugs, vitamins and the like can also be encapsulated in fats and oils. The encapsulation of product additives has certain benefits. The encapsulating substances can act as a taste mask to improve the organoleptic qualities of the food product and also to taste mask certain bitter-tasting drugs. Encapsulating can also prevent unintended volatilization of the actives over time. Furthermore, the substances which encapsulate the drugs can act to deliver them in a time-release fashion.

One technique to provide an encapsulated product matrix is to form the encapsulated product in an extrusion process. An encapsulant such as fat is typically processed in an extruder under controlled heat and pressure. The fat is liquefied or molten and forced through extrusion dies to form round bead or sphere-like particles. Additives may be introduced into the fat during the extrusion process so that the small formed beads include the additive encapsulated within the fat.

This extrusion process serves adequately for many products in the food and pharmaceutical industries. However, the method has certain limitations. In an extrusion process, it is difficult to obtain high loading of the additive material into the fat spheres. The process itself limits the amount of additive which can be introduced into the oleaginous material as the product undergoes extrusion. Further, certain additives which are desirable to be encapsulated with fat exhibit an extremely low melt point. Thus, during the heated extrusion process these low melt additives may have a tendency to break down, or degrade. Additionally, certain desirable additives are resistant to melt flow. Thus these additives are especially difficult to incorporate into a fat sphere during a heated extrusion process. Furthermore, the high heat which must be applied in the extrusion process may have a tendency to effect a reduction in the flavor quality of certain additives. Thus, it may be appreciated that certain additives are not particularly well-adapted to being processed in an extrusion process.

In addition, the necessity of first spraying liquid emulsions, and then encapsulating them via an extrusion process of ten necessitates two or even more separate and distinct pieces of equipment. Distinct equipment such as spray dryers, congealers, fluidizers, extruders and evaporators translates into additional overhead and processing costs. Therefore, it is desirable to provide a process for manufacturing fat encapsulated additives wherein the additives retain desirable product qualities and do not deteriorate during the material processing. It is furthermore highly desirable to accomplish this with one self-contained piece of equipment.

SUMMARY OF THE INVENTION

It is an object of the present invention to provide a method and apparatus for forming a product matrix here a product additive may be efficiently encapsulated with one or more encapsulating material.

It is a further object of the present invention to provide a method and apparatus where a product additive may be encapsulated with one or more oleaginous materials and such process does not result in a deterioration of quality of the additive.

A further object in the present invention to provide an apparatus for affecting the encapsulation of a product additive with a sphere or bead of an oleaginous material such as fats or oils.

Still another object of the invention is to provide encapsulated material with increased loading of the additive or active, high content uniformity, enhanced dispersion of the encapsulations in various media, improved taste or taste masking of the encapsulated material, and no or substantially reduced water and microbial activity.

In the efficient attainment of these other objects, the present invention provides a method for forming a product matrix. The method includes the delivery of a substantially solid additive into a free-flow condition. The substantially solid matrix additive is encapsulated during the free-flow condition with a matrix encapsulant which is also supplied to the free-flow condition. The encapsulated additive may also be cooled during the free-flow condition to form the product matrix.

The present invention further provides an apparatus for forming an encapsulated product matrix. The apparatus includes a delivery device that places a product additive into a feedstream of substantially solid particles. A product encapsulant is also delivered into the feedstream of the substantially solid particles to encapsulate the particles. A cooling device may also be employed for cooling the encapsulated solid particles in the feedstream if desired.

In a preferred embodiment shown by way of example herein, a processing tower or other containment environment which has a sufficient free-flow volume is employed. The processing tower accommodates a delivery device at one end thereof so as to eject, deliver or otherwise place the product additive into a free-flow condition within the free-floe containment volume. An encapsulant delivery device ejects, or otherwise delivers the product encapsulant into the free-flow stream so as to encapsulate the individual particles therein. The encapsulated particles remain in a free-flow condition for a sufficient amount of time to form the product matrix.

In one especially preferred embodiment of the invention, the processing tower apparatus may be modified to include additional entry ports for inclusion of double, or even triple or more, the quantity of material to be encapsulated. The product additive delivery device for delivering particles of the product additive into the free-flow condition can be located towards either end of the free-flow containment environment or tower. The equipment will therefore permit differing types of material to encapsulate or to be encapsulated to separately enter the apparatus.

In still another embodiment, it is also desirable to include additional entry ports for the inclusion of an increased quantity of oleaginous encapsulating material entering the processing tower, as well provide for the entry of differing encapsulating materials.

Overall, the invention provides an encapsulated product matrix in which both the types of material to be encapsulated and the encapsulating materials themselves can be optimized according to whatever requirements are necessary in the final product without the need to utilize additional apparatus or to stop and clean the instant inventive apparatus.

DETAILED DESCRIPTION OF THE PREFERRED EMBODIMENTS

Figure 1:
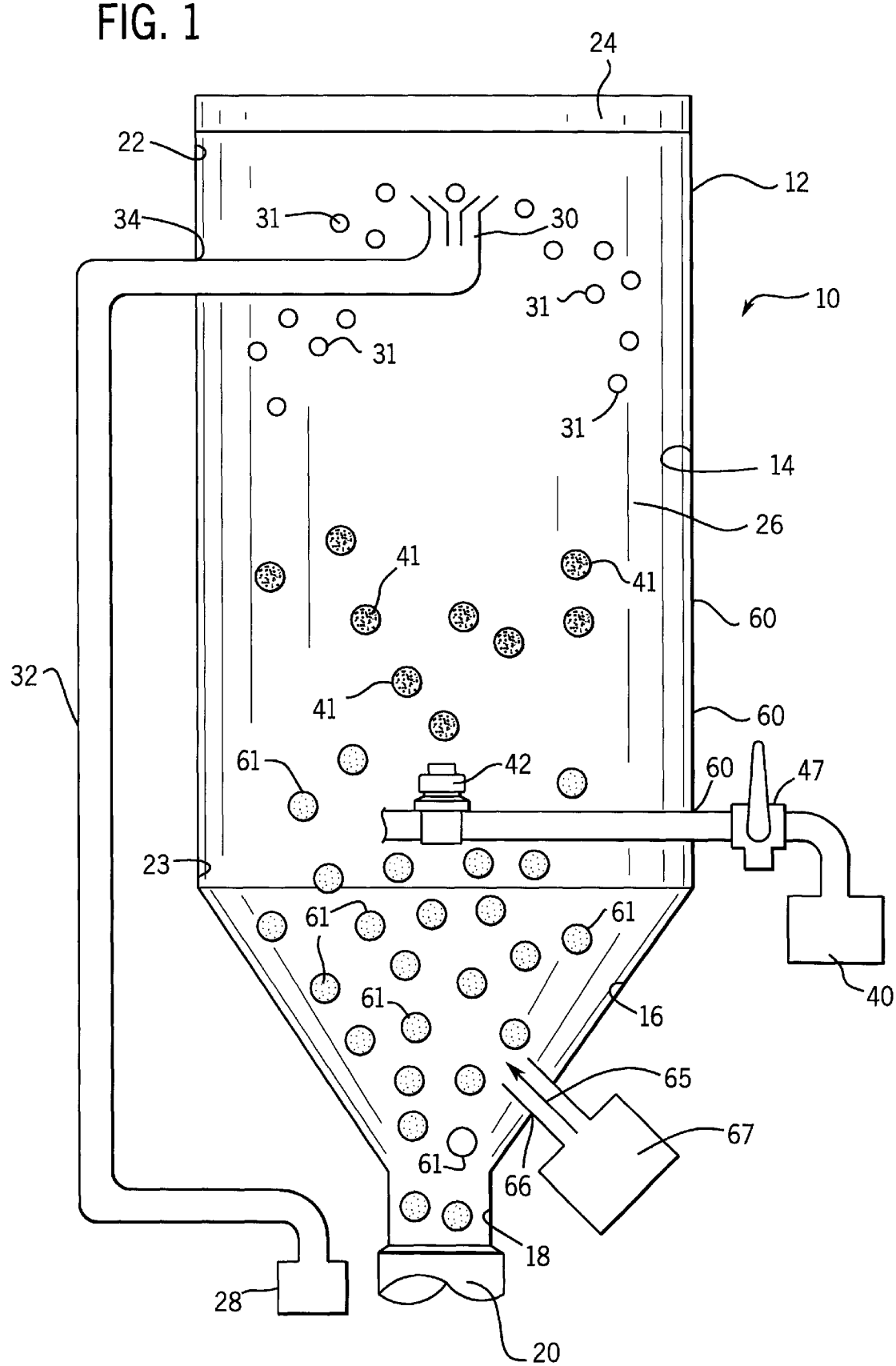
FIG. 1 is schematic representation of the product encapsulating apparatus of the present invention.

The present invention is directed to method and apparatus for forming an encapsulated feedstock product matrix. The resultant product matrix is preferably in the form of tiny particles in the shape of beads or spheres, though variations thereof are certainly within the scope of the invention. Each of the sphere-like particles includes particles of a matrix additive (material to be encapsulated) which are enrobed with spheres or tiny masses of an encapsulating material.

In the present illustrative embodiment, the product additives may include flavors, fibers, colorings, sugars and other additives useful in the manufacture of food-stuffs, and especially confectionery products such as gums, candies, lozenges and mints, etc and combinations thereof. Also highly suitable are actives, i.e. those materials which are intended to produce a biological, chemical or pharmacological, etc. response once ingested. Thus, drugs, vitamins, minerals, nutraceutcials and other dietary supplement material are within the scope of materials to be encapsulated. Especially suitable are actives with undesirable organoleptic qualities such as bitter taste or offensive odor. By encapsulating these materials to form a product matrix, their off-taste can be successfully masked, while their efficacy is preserved until ingestion.

The encapsulating material or materials may include a dissimilar material such as an oleaginous material like various fats or oils and including vegetable oils, soy bean oil, cannola oil, corn oil, cocoa butter, sunflower oil, animal fats, tallows, lards, fish oils, crustation oils, and mixtures thereof. Also useful are medium chain triglycerides, and other substances with fatty moieties. Materials with emulsifying capabilities are also highly desirable. Particularly preferred may be natural and synthetic flavor oils, including without limitation, such oils as a spearmint, peppermint, menthol, wintergreen, cinnamon and citrus oils. This encapsulating material can also have incorporated thereinto other additives such as bioaffecting agents, dyes, fragrances, crystallization modifiers, surfactants, control agents, sweeteners, flavors and mixtures thereof. Certain of these additional additives, which are directly introduced into the oleaginous material, are typically of the type which may be subjected to fairly high temperature environments without degradation of product qualities. It is also within the scope of the invention that the encapsulating material in fact be substantially or wholly a proteinaceous substance or carbohydrate-based. Thus, while it is preferred that the encapsulating material be oleaginous, it is certainly expected that other types of material available to the skilled artisan be employed as well. For the purposes herein, the term "oleaginous" is intended to cover all such materials.

The present invention permits the incorporation of certain other additives of the type described above which would be subject to product degradation if combined with oleaginous material in a conventional high-heat extrusion process. Thus, the present invention is directed to the incorporation of certain product additives into extruded oleaginous spheres without degradation of the beneficial attributes of the additive.

Referring now to FIG. 1, a schematic representation of the method and apparatus of the present invention is shown. A product encapsulating apparatus 10 of the present invention is shown. Encapsulating apparatus 10 includes a free flow containment device 12. The free flow containment device is preferably a tower apparatus 12, but those skilled in the art will recognize that any device which can contain, suspend, fluidize and/or separate the additives and encapsulating material may be utilized. As shown in FIG. 1, the preferred tower 12 is generally an elongate enclosure container having cylindrical side wall 14 in communication with a lower frustro-conical end wall 16. Frustro-conical end wall 16 has a lower open end 18 which is in communication with a collection hopper 20. The upper end 22 of tower 12 may be closed by a cap 24 to provide a substantially seated tower interior 26. While an elongate generally cylindrical tower is shown in the present illustrative embodiment, it may be appreciated that any enclosure of suitable dimension my be employed in combination with the present invention. In the present embodiment, tower 12 has a cylindrical wall 14 of an extended length (approximately 5 ft.) for purposes which will be discussed in further detail hereinbelow.

As shown in FIG. 1, encapsulating apparatus 10 includes a source 28 of product additive to be encapsulated. This source 28 can include any device capable of delivering material into the tower 12. For example, the delivery source 28 may be a supply ejector, or a spinning head apparatus, such as that described in U.S. Pat. Nos. 5,427,811, 5,445, 769, 5,447,423, 5,458,823 and most recently, U.S. Pat. No. 5,834,033. In a preferred embodiment shown in FIG. 1, the product source 28 is a spray dry device. Dry spray device 28 includes a dry spray nozzle 30 supported within the interior 26 of tower 12 adjacent the upper end 22 thereof using any means known in the art. Dry spray nozzle 30 is in communication with a product conduit 32 for delivering liquid or semi-liquid product (in one embodiment liquid product emulsion) to the spray nozzle 30. The conduit 32 may be formed of an insulated pipe which delivers the liquid material from a location where the liquid material is prepared (not shown) to the spray nozzle 30 within interior 26 of tower 12. Entry port 34 is provided at the upper end of tower 12 through cylindrical side wall 14 so as to permit delivery of the liquid product to the spray nozzle 30 within tower 12.

Dry spray apparatus 28 can be of conventional construction and is desirably used to dry out excess moisture in the liquid product and convert the liquid product to a dry powder at relatively high temperatures. Those skilled in the art will discover that the product does not have to be dry upon entering the tower via conduit 32, however (the material may be wet and subsequently be either partially or wholly dried upon exposure to the air or other gaseous medium inside the tower 12, or in some instances may even remain in a liquid or semi-liquid state upon entering the interior of the tower). Dry spray apparatus 28 may be operational under electrical power and may heat the emulsion by gas, steam or electrical energy. Conventional feeding pumps (not shown) are used to deliver the liquid from a location adjacent the lower end of tower 12 to the spray nozzle 30 located interior of the upper end of tower 12. The emulsion which is delivered by conduit 32 includes an emulsion of a product additive as above-described.

The dry spray nozzle 30 operates in a conventional fashion to convert the liquid product to a dried power and spray eject solid powered particles 31 into a feedstream of such particles in a free-flow condition. The dried particles 31 drop under the influence of gravity through the tower interior 26 in such free-flow condition. It is also within the scope heretofore described that the additive material contain a "drying" material recognized by those skilled in the art. For example, cellulosic material may be utilized to imbibe and absorb excess moisture which might otherwise contaminate the product additive. In this way, any drying action of the dry spray apparatus 28 may be augmented or even replaced.

Encapsulating apparatus 10 of the present invention further includes an encapsulation extruding device 40. Extruding device 40 delivers an extruded liquid or semi-liquid encapsulating material, preferably oleaginous material such as one or more fats or oils, to an extrusion nozzle 42 which is supported within the interior 26 of tower 12 adjacent the lower end 23 thereof. Preferably, the encapsulating material is at an elevated temperature. The extruder serves to eject extruded oleaginous beads or spheres 41 into the interior 26 of tower 12. Formation of such fat or oil spheres with extruding device 40 may be accomplished preferably in accordance with a method and apparatus disclosed in commonly assigned U.S. Pat. No. 5,380,473 entitled "Process For Making Shear Form Matrix". The process and apparatus disclosed therein forms a shear-form matrix by raising the temperature of the oleaginous material to a point where the material undergoes internal flow upon application of a fluid shear force, but at a temperature typically below the melting point of the material. The material is advanced and ejected while in this internal flow condition and subjected to a disruptive fluid shear force to form multiple parts or masses which have a sphere or bead-like configuration. The multiple masses are cooled substantially immediately after contact with the disruptive shear force and are ejected into a feedstream into a free-flow condition and solidified. The disruptive force is applied to the oleaginous material abruptly over a short period of time so that the duration of the disruptive force can be considered instantaneous. The oleaginous material can be subjected to a stream of fluid, gas or liquid impacting the material at a velocity which creates the flash disruptive shear force. In the present embodiment, the preferred fluid is air. However, other types of fluids may be used to create the fluid shear force. In a specific embodiment, air is ejected against the material as a continuous high velocity jet. The pat of the material is abruptly disrupted into discrete continuous masses or spheres due to the shear acting on the material while it has internal flow.

Figure 2:
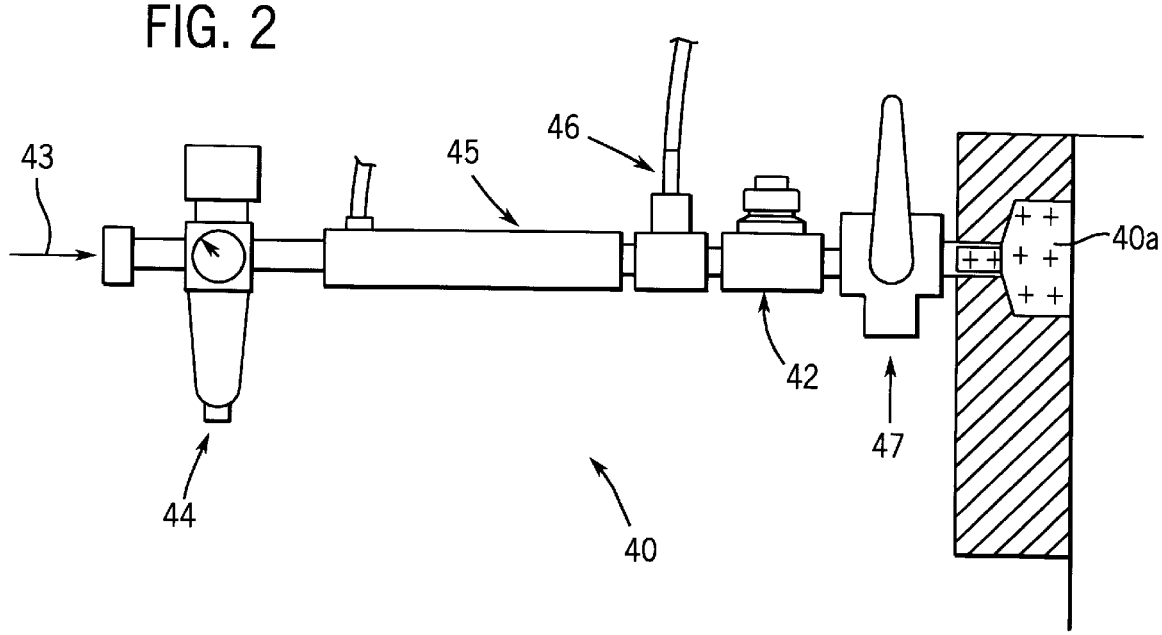
FIG. 2 is a schematic representation of an encapsulant extruder used in accordance with the present invention.

Referring now to FIG. 2, in the extruding device 40 of the preferred embodiment, shear is provided to the extruded encapsulating material 40a while in the internal flow condition by directing a stream of high velocity air against the coherent stream exiting the nozzle 42. The high velocity air can be provided by air stream 43 which can pass through a filter and pressure/flow regulator 44 to an in-line heater 45 and a thermo-couple 46 to control the temperature of the air. The in-line heater 45 can be used to raise the temperature of the air to enhance the free-flow feature of the sheared masses separated from the feedstock stream. Preferably, the air is heated to a temperature of about 75 to 90° C. Those skilled in the art will appreciate that this temperature will vary, depending upon the particular material to be extruded. Any pre-extrusion additives can be introduced with a static mixer 47.

Figure 3:
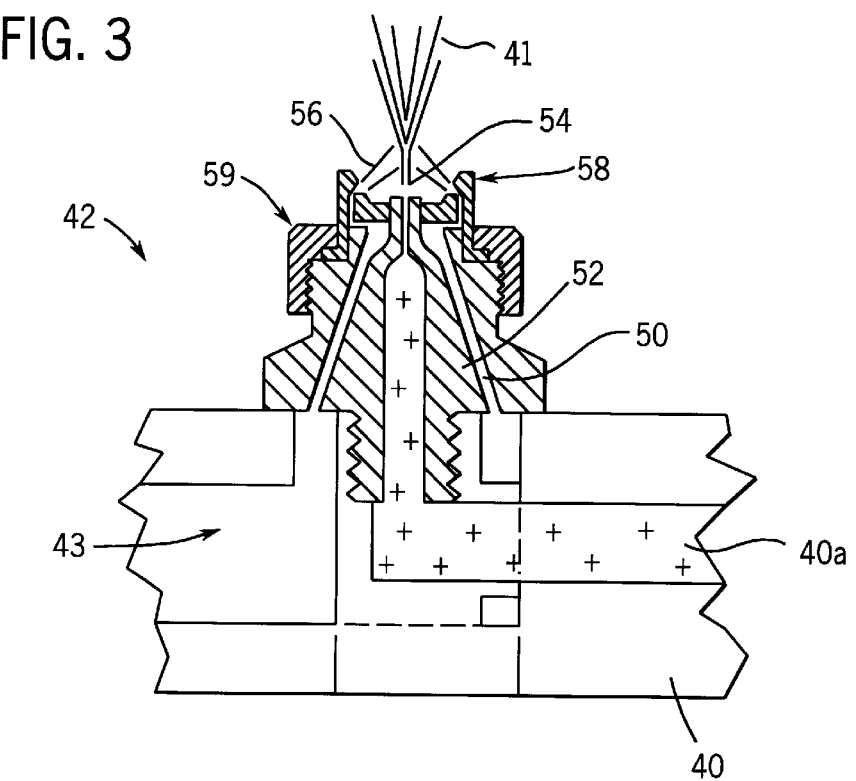
FIG. 3 is a detailed schematic representation of an ejection nozzle of the extruder of FIG. 2.

The stream of air is directed against the extruded encapsulant exterior by the nozzle 42 to provide discontinuities in the encapsulant and basically transform the morphology of the original encapsulant to a new morphology achieved by free-flow solidification as discontinuous masses such as spheres or beads. Referring to FIG. 3, air stream 43 is seen as being in fluid communication with annular channel 50 which surrounds the internal nozzle device 52. Extruded encapsulant material 40a is shown being fed to the nozzle device 52 and exiting as a coherent feedstream 54 where it is subjected to high-velocity air stream 56 which is created by the combination of tortuous path exits provided by air cap 58 and retaining ring 59. In the present embodiment, the coherent feedstream is formed of beads of spheres 41 of encapsulating material. As shown in FIG. 1, such spheres 41 are preferably ejected upwardly in a free-flow condition. In other embodiments, the spheres 41 may be ejected sideways or even downwards from nozzle 42, should such conditions optimize the formation of encapsulated product additive matrices according to the needs of the person skilled in the art.

When air is used to create the shear force, it is applied in a two-fluid nozzle at a pressure of from about 1.5 to about 20 atmospheres. Preferably, the pressure is applied at about 4–6 atmospheres. As previously mentioned, the temperature of the air used to create the shear force should preferably be controlled to a temperature at least about 0.1° C. the temperature of the feedstock being ejected for every atmosphere of pressure.

Referring again to FIG. 1, the extruding device 40 is arranged with respect to tower 12 such that the nozzle 42 is positioned below the dry spray nozzle 30. Thus, the extrusion nozzle 42 is positioned within the feedstream of the ejected solid particles 31 in free-flow condition. The extruding device 40 is arranged so that the extrusion nozzle 42 is directed preferably upwardly so as to eject spheres 41 directly into the gravity fed free-flow feedstream of particles 31 ejected from dry spray nozzle 30. By directing the nozzle 42 upwards, it has been found that the solid particles 31 are often better encapsulated. Preferably, the nozzle will be directed at about 90 degrees upwards (as shown in FIG. 1), with variations thereof of less than about +/−45 degrees, more preferably +/−25 degrees, and even more preferably about +/−10 degrees or even less. Further optimization is attainable according to the particular needs of the skilled technician.

The extruding nozzle 42 may also be positioned at a desirable spaced apart location with respect to nozzle 30. In that regard, tower 12 provides multiple entry ports 60 along the length of cylindrical side wall 14. The location of the extruding nozzle 42 with respect to the dry spray nozzle 30 may be adjusted depending upon the type(s) of material(s) being processed. The position of the extruding nozzle 42 may be varied to control the contact between particles 31 in the free-flow and the ejected spheres 41. Factors such as time of free-flow, temperature and the like are considered when positioning nozzle 42 of extruding device 40 with respect to nozzle 30 of dry spray device 28. In addition, the multiple entry ports 60 can accommodate more than one extruding nozzle 42 at a time. Two or more extruding nozzles may therefore be positioned within the tower 12 at spatially optimal locations (horizontally (x), vertically (y) and laterally(z)) according to the needs of the skilled artisan.

As the fat spheres 41 are ejected so as to come into contact with the dry spray particles 31 in the free-flow condition, the fat spheres are caused to encapsulate the dry spray particles so as to form an encapsulated product matrix 61 of product particles encapsulated with fat spheres. The encapsulated product matrix continues in a free-flow condition under gravity through the lower end 23 of tower 12 and into the frustro-conical wall 16 which funnels the encapsulated product matrix to opening 18 for collection within a hopper 20.

During the free-flow condition, the encapsulated product matrix 61 is preferably subjected to a stream of gaseous fluid so as to solidify the encapsulated product matrix 61. The gaseous fluid is preferably air, but may also comprise any other substantially inert gas. In a preferred embodiment, the gaseous fluid is an air stream. The gaseous fluid may be heated or cooled, or may also be at room temperature, depending upon the type of drying and free-fall conditions required within the tower 12. An air flow pattern may also be utilized to recirculate the encapsulated particles to another part of the tower 12 or to a location outside the tower. A preferred embodiment is set forth in FIG. 1. Cold air stream 65 is introduced into the interior 26 of tower 12 through an air entry port 66 through the frustro-conical wall 16. The entry port 66 is desirably located near the bottom of the tower 12, but it is also within the scope of the invention to optimize location at or near the midpoint or even the top of the tower to take full advantage of fluid dynamics. The air is generated by an air generating device 67 which maintains a cool dry air stream through the entry port. The air stream is preferably supplied within a temperature range of between about 5° to 10° C. and a relatively dry humidity, preferably that of about 25% relative humidity or less, more preferably about 10% relative humidity or less, and even more desirably about 5% or less. In this way, there is less water and consequently less microbial activity in the encapsulated product matrix 61.

Once the encapsulated matrix 61 is cooled and solidified, the matrix particles 61 fall through the frustro-conical wall 16 to the lower open end 18. The air pattern heretofore described can optimize the free-fall conditions of the encapsulated matrices through creation of positive or negative pressure flows, or merely through assistance of the natural forces of gravity. After passing through the lower open end 18, the encapsulated particles are collected within collection hopper 20 for further processing. The encapsulated matrix material may be in solid form, but may also be in semi-solid form, and is preferably in the shape of tiny spheres, beads or solloids.

Figure 4:
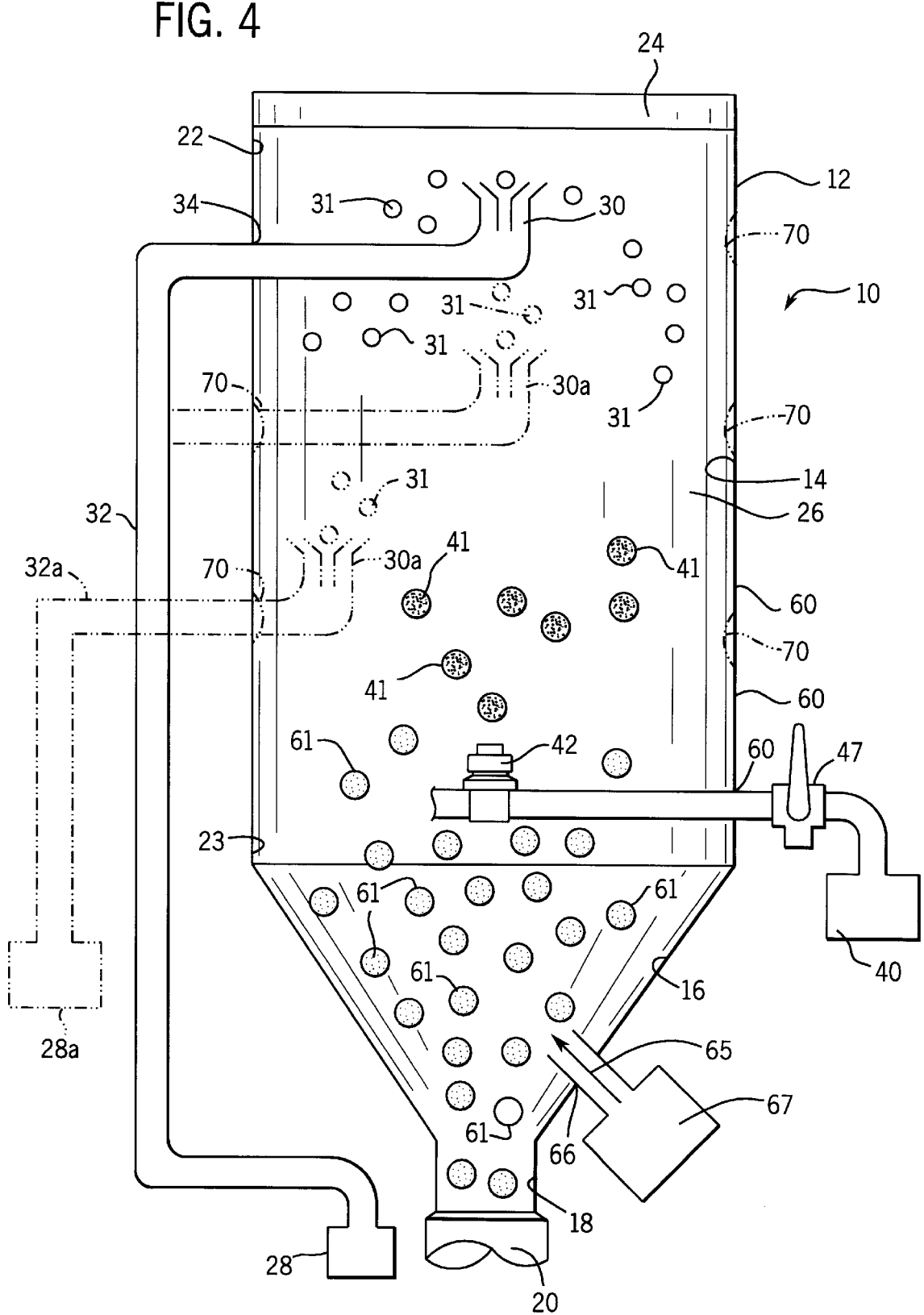
FIG. 4 is a further embodiment of the apparatus shown in FIG. 1.

Referring now to FIG. 4, there is shown a variation of the device set forth in FIG. 1. Encapsulating apparatus 10 is shown with optional additional entry ports 70. In one embodiment, these entry ports allow for introduction of additional particles 31 via components 28 and 32. The various levels of entry of the additional ports 70 shown in FIG. 1, as well as their respective orientations, may be adjusted by the skilled artisan to account for variations in the physical properties of the material 31 itself, e.g. weight, density, thickness, etc. In another embodiment of the invention, the entry ports 70 may also be utilized to admit material 31 to the apparatus 10 from another source 28a, 30a and 32a shown in FIG. 4. In this way, double or even triple the amount of material may be added to the apparatus 10 at the same time, or two or more separate and distinct materials may be added for encapsulation. The materials 31 may be added simultaneously or in sequence. The various heights of the additional entry ports 70 may be utilized so that one material is encapsulated first, and a second material (which is introduced at a lower or higher level) is next encapsulated. This procedure may be especially relevant when the materials to be encapsulated are particularly reactive with one another. The oleaginous material encapsulates both materials during free fall, and at the same time, can keep them physically apart from one another. It is within the skilled artisan's judgment to decide how many additional entry ports 70 to utilize, as well as their relative locations. It is also possible to adjust the direction of the nozzle(s) 30. For example, one or more could be directed upwards (as shown in the Figures), but one or more could also be directed sideways or downwards as well, to thereby operate in the most efficient way with respect to one another. In this way, the skilled artisan may be further able to regulate and maximize optimal conditions for encapsulation according to his or her needs.

Figure 5:
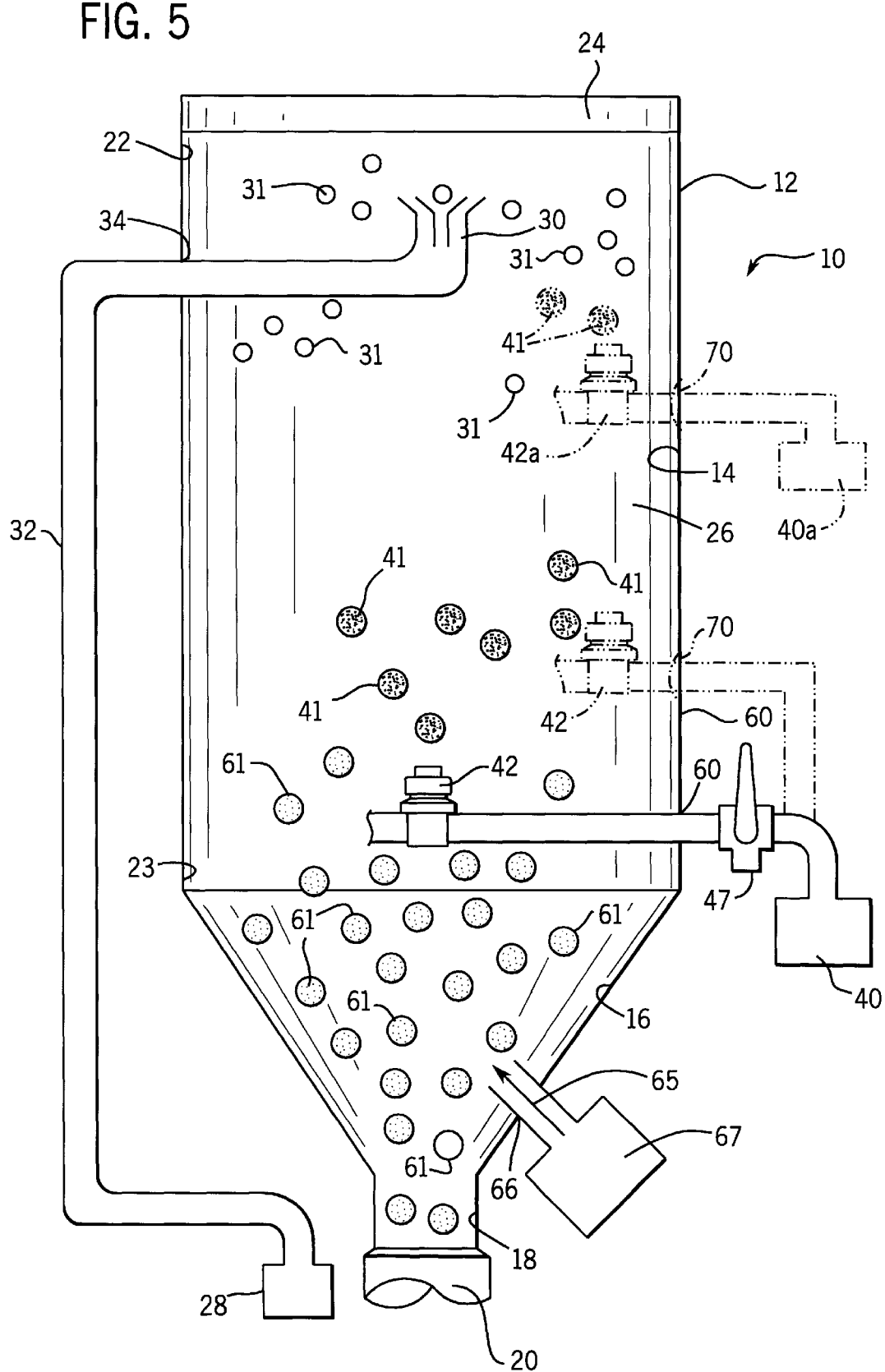
FIG. 5 is still another embodiment of the apparatus shown in FIG. 1.

A still further aspect of the invention is set forth in FIG. 5. As shown in FIG. 5, there are additional entry ports 70 provided for entry of oleaginous encapsulating material 41 via components 40 and 42. In this way, it is possible to double or even triple etc. the amount of encapsulating material 41 entering the apparatus 10, or take full advantage of two differing angles for entry to further ensure complete encapsulation. It is also within the scope of the invention that two or more distinct oleaginous encapsulating materials be added at the same time via additional components 40a and 42a shown in FIG. 5, for example. It is further possible to add one type of oleaginous encapsulating material through one entry port 70, and a second (or third, etc.) oleaginous encapsulating material thereafter through another entry port, whether simultaneously or in succession. As heretofore described as well, one or more of the nozzles 42 may be directed upwards, while at the same time one or more may be directed sideways or even downwards as well.

It is further within the scope of the invention that the embodiments shown in FIGS. 4 and 5 be utilized in conjunction with one another. Optimization of the particular embodiments is possible, depending upon the type and quantity of material(s) to be encapsulated, as well as the type and quantity of encapsulating material to be utilized.

Additional entry ports 70 may also be utilized to adjust the relative positions of the components 30 and 42 with respect to one another. When one or more of the entry ports 70 is not in use, it may simply be covered.

By virtue of the invention according to the embodiments herein described, it is possible to provide encapsulated material without the need for several distinct pieces of equipment. The method herein described provides excellent product which can be utilized in a wide range of applications. The encapsulated material as a result of the novel process is a matrix in which there is intimate mixing of dissimilar ingredients such as sugars and oils. It is also possible to attain increased loading of the additives which are encapsulated compared to other processes known in the art such as standard spray drying and spray congealing techniques. Thus, it is possible to attain about 40–60% loading of additives or actives without any adverse effects. A conventional spray dryer many times can attain only about 20% loading. A further advantage of the invention is enhanced product uniformity; there is often considerably less variance in content within the same batch and even after several batches of processed material. Enhanced dispersion of the encapsulated product matrix in further media such as, for example, standard chewing gum bases is also attainable. The drying process of the invention is furthermore unique in that the encapsulated product also exhibits a lowered water activity and microbial activity as compared to other encapsulations available today. In addition, the encapsulated product matrix exhibits excellent taste-masking in certain embodiments and improved taste in others.

As heretofore described, other embodiments of the device of the invention are possible. In one such embodiment, the tower 12 may be replaced with a sideways T-shaped tube in which air is circulated via the two stems of the "T" and both additive material and encapsulating material enter via the main portion of the "T" and are brought together by the action of the air flow. In another embodiment, a tube-within-a-tube design permits air circulation and introduction of material into the interior tube. Upon mixing under the force of the circulating air, the encapsulated product matrices exit into the exterior tube for collection.

EXAMPLES

The following examples illustrate various preferred embodiments of the invention. These should not be construed as limiting the scope thereof, however.

Example 1

In this example, the device set forth in FIG. 1 was utilized to form an encapsulated product matrix. A peppermint/spearmint flavor combination and sucrose mixture was encapsulated using peppermint oil (an oleaginous material). The resultant product matrix was a substantial quantity of large spheres that were dry to the touch. When sampled, the spheres revealed an intense mint taste. Little of the mint sensation could be detected, however, with the nostrils, indicating that the peppermint/spearmint flavors were well encapsulated and preserved within the matrix. The product matrix spheres were then combined with gum base in a traditional manner, along with other chewing gum additives. The final chewing gum product provided a sweet minty chewing sensation, which due to the encapsulated product matrix throughout the gum base, was intense and long-lasting for over 30 minutes.

Example 2

For this example, a bitter tasting medicament (ibuprofen) was successfully encapsulated using spearmint oil. When combined into a confectionery base having a soft and chewy consistency, the resultant product yielded a delivery system in which medicine could be palatably administered without off-taste, thereby substantially increasing patient compliance.

Various changes to the foregoing described and shown structures would now be evident to those skilled in the art. Accordingly, the particularly disclosed scope of the invention is set forth in the following claims.

What is claimed is:

1. A method of forming a product matrix comprising the steps of:

ejecting a substantially solid matrix additive upwardly through a nozzle such that said matrix additive then descends into a free-fall condition;

encapsulating said ejected solid matrix additive at said free-fall condition with a matrix encapsulant at a location below that of where said matrix additive is ejected, said matrix encapsulant being ejected upwardly into said free-falling matrix additive at a location below that of where said matrix additive is ejected upwards; and allowing said encapsulated additive to substantially solidify in said free-fall condition to form said product matrix, wherein said method is effected within one self-contained piece of equipment.

2. A method of claim 1 wherein said matrix encapsulant has been heated to induce internal flow thereof.

3. A method of claim 2 wherein said matrix encapsulant has been ejected from an extruding device and subjected to disruptive fluid shear force.

4. A method of claim 1 further comprising the step of applying a cold air stream to said product matrix.

5. A method of claim 1 wherein said solid matrix additive is ejected upwardly at at least two locations within said equipment.

6. A method of claim 1 further comprising the ejection of at least one additional solid matrix additive within said equipment.

7. A method of claim 1 further comprising the ejection of at least one additional matrix encapsulant within said equipment.

8. A method of claim 1 wherein said matrix encapsulant is an oleaginous material.

9. A method of claim 8 wherein said oleaginous material is at least one member selected from the group consisting of animal and vegetable oils and fats, and natural and synthetic flavor oils.

10. A method of claim 9 wherein matrix additive is at least one member selected from the group consisting of flavors, fibers, colorings, sugars, drugs, vitamins, minerals and nutraceuticals.

11. A method of claim 10 wherein said matrix additive is selected from the group consisting of sugars.

12. A method of claim 1 wherein said matrix encapsulant is introduced into said equipment at a location below that of said matrix additive.

13. The method of claim 11, said solid matrix additive is converted from a liquid to a solid state prior to exiting said nozzle.

* * * * *